United States Patent [19]

Zimmerman

[11] Patent Number: 5,216,154
[45] Date of Patent: Jun. 1, 1993

[54] PROCESS FOR THE PREPARATION OF N-METHYLMORPHOLINE OXIDE

[75] Inventor: Robert L. Zimmerman, Austin, Tex.

[73] Assignee: Texaco Chemical Company, White Plains, N.Y.

[21] Appl. No.: 825,898

[22] Filed: Jan. 27, 1992

[51] Int. Cl.$^5$ ............................................ C07D 295/24
[52] U.S. Cl. ................................................... 544/173
[58] Field of Search ........................................ 544/173

[56] References Cited

PUBLICATIONS

EPA 0 307 184 (Bauer et al.) (Mar. 1989) Chem. Abts. 111:114,735.

*Primary Examiner*—Robert W. Ramsuer
*Attorney, Agent, or Firm*—James L. Bailey; Kenneth R. Priem; Carl G. Ries

[57] ABSTRACT

N-methylmorpholine oxide which is essentially free from nitrosamine contaminants is prepared by oxidizing a feedstock consisting essentially of N-methylmorpholine with an oxidant consisting essentially of aqueous hydrogen peroxide in an atmosphere consisting essentially of carbon dioxide to thereby form a nitrosamine-free reaction product from which N-methylmorpholine oxide essentially free from nitrosamine can be recovered.

1 Claim, No Drawings

PROCESS FOR THE PREPARATION OF N-METHYLMORPHOLINE OXIDE

BACKGROUND OF THE INVENTION

1. Technical Field of the Invention

This invention relates to a method for the production of N-methylmorpholine oxide. More particularly, this invention relates to a method wherein N-methylmorpholine is reacted with aqueous hydrogen peroxide in an atmosphere consisting essentially of carbon dioxide in order to provide a reaction product consisting essentially of N-methylmorpholine oxide, the reaction product being contaminated with less than 25 parts per billion of nitrosamine impurities.

2. Prior Art

Bauer et al. European patent application 0,307,184, filed Jul. 9, 1988, discloses a method for the preparation of tertiary amine oxides substantially free from nitrosamine byproducts wherein a tertiary amine is reacted with aqueous hydrogen peroxide in the presence of carbon dioxide at a temperature of 45° C. or less. The preferred amine starting materials are alkyl amines. N-methyl morpholine is mentioned, but there is no mention of the discovery herein that N-methyl morpholine is a unique feedstock in that N-methyl morpholine oxide substantially free from nitrosamine by-products can be prepared by reacting N-methyl morpholine with hydrogen peroxide in the presence of carbon dioxide at reaction temperatures of 50° to 100° C.

Murata et al. U.S. Pat. No. 4,247,480 is directed to a method for the preparation of amine oxides wherein a tertiary amine is oxidized in the presence of carbon dioxide and a promoter such as ethylenediaminetetraacetic acid, stanates, polyphosphates, etc. The oxidant that is used is hydrogen peroxide.

Bauer et al. U.S. Pat. No. 4,994,614 is also directed to a process for the preparation of tertiary amine oxides by the reaction of a tertiary amine with hydrogen peroxide in the presence of carbon dioxide and ascorbic acid. The stated advantage of the process is the provision of tertiary amine oxides that are substantially free from nitrosamine byproducts. It is stated that the results were unexpected because under the same reaction conditions amine oxides made in the presence of either carbon dioxide or ascorbic acid individually contain significant quantities of nitrosamines. A wide variety of tertiary amines are mentioned as feedstocks including dialkyl amines, triaryl amines, mixed alkyl aryl, alkyl-arylalkyl, aryl-arylalkyl or alkyl-aryl-arylalkylamines including also heterocyclic amines such as N-methyl piperidine, N,N'-dimethyl piperazine, pyridine, 2-methyl pyridine, N-methyl pyrrolidine, N-methyl pyrrolidone, N-methyl morpholine, N-ethyl morpholine, and the like.

European Patent Application No. 0,356,918 discloses a process for preparing amine oxides having decreased levels of nitrosamine contamination by reacting a tertiary amine with hydrogen peroxide in the presence of titanium alone or in the combined presence of titanium and carbon dioxide.

European Patent No. 0,409,043 discloses a process for the preparation of amine oxides having reduced nitrosamine contamination by the reaction of a tertiary amine with hydrogen peroxide in the presence of alkyleneaminopoly(methylenephosphonic acid).

SUMMARY OF THE INVENTION

It has been surprisingly discovered in accordance with the present invention that when N-methylmorpholine is reacted with aqueous hydrogen peroxide in an atmosphere of carbon dioxide in the absence of other additive materials, there is a substantially quantitative conversion of the N-methylmorpholine to N-methylmorpholine oxide and the product will contain less than about 25 parts per billion of nitrosamine contaminants. The results are particularly surprising because the prior art, as exemplified by the references cited above, teach that it is necessary to use a second catalytic material such as titanium or ascorbic acid in order to obtain a significant reduction in nitrosamine by-product formation even when the reaction is conducted in an atmosphere of carbon dioxide.

Amine oxides are useful in the preparation of shampoos, hair conditioners, dish and laundry detergents, fabric softeners and the like. However, nitrosamines are suspected carcinogens and mutagens and also can contribute a yellow color to the amine oxide product.

It has surprisingly discovered in accordance with the present invention that when N-methylmorpholine is reacted with aqueous hydrogen peroxide in a carbon dioxide atmosphere the resultant product, N-methylmorpholine oxide will have a nitrosamine contamination level of less than about 10 parts per billion.

DESCRIPTION OF THE PREFERRED EMBODIMENT

The starting materials for the preferred embodiment of the present invention are N-methylmorpholine, an aqueous solution of hydrogen peroxide, such as an aqueous solution containing from about 10 to about 55 wt. % of hydrogen peroxide and carbon dioxide. If desired, the hydrogen peroxide can be stabilized with a stabilizer of the type disclosed in European Patent No. 0,409,043, namely, an alkyleneaminopoly(methylenephosphonic acid).

The amount of hydrogen peroxide to be used should be less than the equivalent amount of N-methylmorpholine to be oxidized and, preferably, an excess of N-methyl morpholine is employed. Preferably, from about 0.80 to about 0.99 moles of hydrogen peroxide are used per mole of N-methylmorpholine.

The reaction is suitably conducted at a temperature within the range of about 50° to about 100° C. at a pressure within the range of about 0 to about 100 psig.

EXAMPLES

The invention will be further illustrated by the following examples, which are given by way of illustration and not as limitations on the scope of this invention.

In the following examples, a 2 liter flask equipped with an addition funnel, mechanical stirrer, thermometer and gas sweep were charged with 484.8 g of N-methylmorpholine and 22.5 g of water. To this were added 423.3 g of a 35% aqueous solution of hydrogen peroxide. The reactants were digested to a hydrogen peroxide content of about 0.01 wt. % and then about 60 g of material (N-methylmorpholine and water) were removed under vacuum. The product was then analyzed.

TABLE 1

| Example | I | II | III |
|---|---|---|---|
| Gas used (70 ml/min) | $N_2$ | $CO_2$ | $CO_2$ |

TABLE 1-continued

| Example | I | II | III |
|---|---|---|---|
| Hydrogen Peroxide* | 1 | 1 | 2 |
| Maximum Temperature | 84° C. | 85° C. | 58° C. |
| Digestion Temperature | 65° C. | 65° C. | 53° C. |
| Nitroso Morpholine Content | 4 ppm | <30 PPB | Non Detected |

*Hydrogen Peroxide
1 stabilized as in EN Patent 0,409,043
2 technical grade

Comparing I and II a 100 fold decrease in nitrosamine is seen. This very large change is not expected. Also, in Example III where technical grade hydrogen peroxide was used, no nitrosamine could be detected.

Having thus described my invention, what is claimed is:

1. A method for the preparation of N-methylmorpholine oxide which comprises the steps of:

charging a feed stock consisting essentially of N-methylmorpholine to a reaction vessel and contacting the N-methyl-morpholine therein with a molar excess of an oxidant consisting essentially of technical grade hydrogen peroxide in an atmosphere consisting essentially of carbon dioxide under reaction conditions including a temperature of about 50° to about 100° C. and a pressure of about 0 to 100 psig to thereby form a N-methyl-morpholine oxide reaction product containing less than a detectable amount of nitrosamines, and recovering essentially nitrosamine-free N-methyl-morpholine oxide from the products of the reaction, said technical grade hydrogen peroxide being charged to said reaction vessel as an aqueous solution free from alkyleneaminopoly(methylene-phosphonic acid) stabilizers and containing about 10 to 55 wt. % of hydrogen peroxide.

* * * * *